United States Patent
Charles

(10) Patent No.: US 12,053,244 B2
(45) Date of Patent: Aug. 6, 2024

(54) HEAD TRACKING CONTROL FOR OPHTHALMIC SURGERY

(71) Applicant: Alcon Inc., Fribourg (CH)

(72) Inventor: Steven T. Charles, Memphis, TN (US)

(73) Assignee: Alcon Inc., Fribourg (CH)

( * ) Notice: Subject to any disclaimer, the term of this patent is extended or adjusted under 35 U.S.C. 154(b) by 893 days.

(21) Appl. No.: 17/127,591

(22) Filed: Dec. 18, 2020

(65) Prior Publication Data

US 2021/0186624 A1    Jun. 24, 2021

Related U.S. Application Data

(60) Provisional application No. 62/950,420, filed on Dec. 19, 2019.

(51) Int. Cl.
*A61B 34/20* (2016.01)
*A61B 90/20* (2016.01)
(Continued)

(52) U.S. Cl.
CPC .............. *A61B 34/20* (2016.02); *A61B 90/20* (2016.02); *A61F 9/007* (2013.01); *G06T 7/246* (2017.01);
(Continued)

(58) Field of Classification Search
CPC .................. A61B 34/20; A61B 90/20; A61B 2017/00216; A61B 2017/00221; A61B 2034/2048; A61B 2034/2057; A61B 2034/2072; A61B 2090/3979; A61B 2090/502; A61B 5/0022; A61B 2017/00203; A61B 2017/00398; A61B 5/1127; A61B 5/6814; A61B 90/25; A61B 5/1114; A61B 5/163; A61B 3/132;
(Continued)

(56) References Cited

U.S. PATENT DOCUMENTS 5,345,087 A * 9/1994 Luber .................... A61B 34/74
250/203.2
5,825,536 A * 10/1998 Yasunaga ............... G02B 7/001
359/368

(Continued)

FOREIGN PATENT DOCUMENTS

WO    2016090336 A1    6/2016
WO    2019210322 A1    10/2019

*Primary Examiner* — Scott M. Getzow

(57) ABSTRACT

The present disclosure provides a head tracking control system including at least one marker positioned on a head of a surgeon. The system further includes an infrared camera including at least two infrared sensors and that detects infrared light reflected off the at least one marker and sends a signal corresponding to the detected light to a processor, and that executes instructions on the processor to detect a movement of the at least one marker. The system also includes an intelligent tracking system that executes instructions on the processor to determine if the detected movement of the at least one marker corresponds to a defined head movement of the surgeon. The system further includes an ophthalmic surgical microscope including the processor. If the detected movement of the at least one marker corresponds to the defined head movement of the surgeon, the processor executes instructions to control the ophthalmic surgical microscope.

19 Claims, 8 Drawing Sheets

(51) Int. Cl.
    *A61F 9/007*         (2006.01)
    *G06T 7/246*         (2017.01)
    *A61B 17/00*         (2006.01)
    *A61B 90/00*         (2016.01)
    *A61B 90/50*         (2016.01)

(52) U.S. Cl.
    CPC ............... *A61B 2017/00216* (2013.01); *A61B 2017/00221* (2013.01); *A61B 2034/2048* (2016.02); *A61B 2034/2057* (2016.02); *A61B 2034/2072* (2016.02); *A61B 2090/3979* (2016.02); *A61B 2090/502* (2016.02); *G06T 2207/10048* (2013.01); *G06T 2207/30196* (2013.01); *G06T 2207/30204* (2013.01)

(58) Field of Classification Search
    CPC ..................... A61F 9/007; G06T 7/246; G06T 2207/10048; G06T 2207/30196; G06T 2207/30204; G16H 20/40; G16H 40/63
    See application file for complete search history.

(56) References Cited

U.S. PATENT DOCUMENTS

| | | | | |
|---|---|---|---|---|
| 2016/0021304 | A1* | 1/2016 | Osterhout | G06F 3/013 |
| | | | | 348/77 |
| 2016/0225192 | A1 | 8/2016 | Milton et al. | |
| 2017/0319143 | A1* | 11/2017 | Yu | A61B 5/682 |
| 2021/0290433 | A1* | 9/2021 | Sieving | A61N 1/325 |

* cited by examiner

HEAD TRACKING CONTROL FOR OPHTHALMIC SURGERY

TECHNICAL FIELD

The present disclosure relates to ophthalmic surgery and surgical equipment, and more specifically, to a head tracking control system to improve visualization for ophthalmic surgery and associated methods.

BACKGROUND

Ophthalmic surgery is surgery performed on the eye or any part of the eye. Ophthalmic surgery saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

One type of ophthalmic surgery, vitreoretinal surgery, encompasses various delicate procedures involving internal portions of the eye, such as the vitreous humor, the retina, epiretinal membranes, and the internal limiting membrane. Different vitreoretinal surgical procedures are used, sometimes with lasers, to improve visual sensory performance in the treatment of many eye diseases, including epimacular membrane, diabetic retinopathy, vitreous hemorrhage, macular hole, detached retina, vitreomacular traction syndrome, macular schisis, and complications of cataract surgery, among others.

During ophthalmic surgery, such as vitreoretinal surgery, an ophthalmologist typically uses an optical, surgical microscope with oculars to view a magnified image of the eye undergoing surgery. A surgical microscope may provide intraoperative viewing of optical images of an eye, and optionally illumination of the eye for ophthalmic surgery. The patient typically lies supine under the surgical microscope during ophthalmic surgery and a speculum is used to keep the eye exposed. Depending on the type of optical system used, the surgeon has a given field of view of the fundus, which may vary from a narrow field of view to a wide field of view that can extend to peripheral regions of the fundus.

More recently, ophthalmic surgeons may use an ocular-free digital image system to aid visualization during ophthalmic surgery such as NGENUITY® (Novartis AG Corp., Switzerland). These systems may include a 3D high dynamic range ("HDR") camera system with a pair of complementary metal-oxide-semiconductor (CMOS) sensors that allow the surgeon to view the retina on a display screen using polarized glasses, digital oculars or a head-mounted display. The display screen provides relief from having to view the surgery using oculars and allows others in the operating room to see exactly as the surgeon does. The system also allows for improved images under high magnification, and increased depth of field compared to a conventional optical, analog surgical microscope. In addition, an ophthalmic surgical microscope or digital image system may include a foot pedal located on the floor, which may provide for foot-actuated control of various visualization displays during ophthalmic surgery. However, when performing ophthalmic surgery, a hand-, voice-, or foot-actuated command to control displays or equipment may not be desirable or practical.

SUMMARY

The present disclosure provides a head tracking control system that improves visualization for ophthalmic surgery. The head tracking control system includes at least one marker positioned on a head of a surgeon. The head tracking control system also includes an infrared camera including at least two infrared sensors and that detects infrared light reflected off the at least one marker and sends a signal corresponding to the detected light to a processor. The infrared camera also executes instructions on the processor to detect a movement of the at least one marker. The head tracking control system also includes an intelligent tracking system that executes instructions on the processor to determine if the detected movement of the at least one marker corresponds to a defined head movement of the surgeon. The head tracking control system also includes an ophthalmic surgical microscope that includes the processor. If the detected movement of the at least one marker corresponds to the defined head movement of the surgeon, the processor executes instructions to control the ophthalmic surgical microscope.

The head tracking control system and its methods of use may include the following additional features: i) the defined head movement of the surgeon may be a quiet head movement, a deliberate head movement, an uncommon head movement, or any combination thereof; ii) the intelligent tracking system may include a noise detection system that includes a microphone and determines if the detected movement of the at least one marker corresponds to a quiet head movement of the surgeon; a motion thresholding system that determines if the detected movement of the at least one marker corresponds to a deliberate head movement of the surgeon; and a motion recognition system that determines if the detected movement of the at least one marker corresponds to an uncommon head movement of the surgeon; iii) a head movement that is not the defined head movement may be ignored by the head tracking control system; iv) the defined head movement may be a displacement along an x-axis, a displacement along a y-axis, a pitch movement, or any combination thereof; v) the system may further include a motorized microscope head support, and the processor may control the ophthalmic surgical microscope by executing instructions to move the motorized microscope head support along a microscope movement x-axis, a microscope movement y-axis, or any combination thereof; vi) the system may further include an objective, and the processor may control the ophthalmic surgical microscope by executing instructions to move the objective; vii) the at least one marker may be an active infrared marker, a passive infrared marker, a fiducial marker, disposed in a cap, attached by adhesive, marked in pen, or any combination thereof.

The present disclosure further provides a head tracking control system that includes a 3-axis gyroscope and a 3-axis accelerometer positioned on the head of a surgeon and that detect a head movement of the surgeon and send a signal corresponding to the detected movement to a processor. The head tracking control system also includes an intelligent tracking system that executes instructions on the processor to determine if the detected head movement of the surgeon corresponds to a defined head movement of the surgeon. The head tracking control system also includes an ophthalmic surgical microscope that includes the processor. If the detected head movement of the surgeon corresponds to the defined head movement of the surgeon, the processor executes instructions to control the ophthalmic surgical microscope.

The head tracking control system and its methods of use may include the following additional features: i) the defined head movement of the surgeon may be a quiet head movement, a deliberate head movement, an uncommon head movement, or any combination thereof; ii) the intelligent tracking system may include a noise detection system that includes a microphone and determines if the detected head movement of the surgeon corresponds to a quiet head movement; a motion thresholding system that determines if the detected head movement of the surgeon corresponds to a deliberate head movement; and a motion recognition system that determines if the detected head movement of the surgeon corresponds to an uncommon head movement; iii) a head movement that is not the defined head movement may be ignored by the head tracking control system; iv) the defined head movement may be a displacement along an x-axis, a displacement along a y-axis, a pitch movement, or any combination thereof; v) the system may further include a motorized microscope head support, and the processor may control the ophthalmic surgical microscope by executing instructions to move the motorized microscope head support along a microscope movement x-axis, a microscope movement y-axis, or any combination thereof; vi) the system may further include an objective, and the processor may control the ophthalmic surgical microscope by executing instructions to move the objective.

The present disclosure further provides a head tracking control system that includes at least one marker positioned on a head of a surgeon. The head tracking control system also includes an LED driver that emits near-infrared light. The head tracking control system also includes a digital micromirror device that modulates the near-infrared light emitted by the LED driver and projects the modulated light at the at least one marker. The head tracking control system also includes a three-dimensional scanning camera that detects distortions in the modulated light reflected off the at least one marker, sends a signal corresponding to the distortions to a processor, and executes instructions on the processor to detect a movement of the at least one marker. The head tracking control system also includes an intelligent tracking system that executes instructions on the processor to determine if the movement of the at least one marker corresponds to a defined head movement of the surgeon. The head tracking control system also includes an ophthalmic surgical microscope that includes the processor. If the movement of the at least one marker corresponds to the defined head movement of the surgeon, the processor executes instructions to control the ophthalmic surgical microscope.

The head tracking control system and its methods of use may include the following additional features: i) the defined head movement of the surgeon may be a quiet head movement, a deliberate head movement, an uncommon head movement, or any combination thereof; ii) the intelligent tracking system may include a noise detection system that includes a microphone and determines if the detected movement of the at least one marker corresponds to a quiet head movement of the surgeon, a motion thresholding system that determines if the detected movement of the at least one marker corresponds to a deliberate head movement of the surgeon, and a motion recognition system that determines if the detected movement of the at least one marker corresponds to an uncommon head movement of the surgeon; iii) a head movement that is not the defined head movement may be ignored by the head tracking control system; iv) the defined head movement may be a displacement along an x-axis, a displacement along a y-axis, a pitch movement, or any combination thereof; v) the system may further include a motorized microscope head support, and the processor may control the ophthalmic surgical microscope by executing instructions to move the motorized microscope head support along a microscope movement x-axis, a microscope movement y-axis, or any combination thereof; vi) the system may further include an objective, and the processor may control the ophthalmic surgical microscope by executing instructions to move the objective; vii) the at least one marker may be an active infrared marker, a passive infrared marker, a fiducial marker, disposed in a cap, attached by adhesive, marked in pen, or any combination thereof.

The present disclosure further provides a visualization system that includes a head tracking control system including a processor and at least one marker positioned on a head of a surgeon. The visualization system further includes a surgeon head movement detection device that detects infrared light reflected off the at least one marker and sends a signal corresponding to the detected light to the processor, and executes instructions on the processor to detect a movement of the at least one marker. The visualization system further includes an intelligent tracking system that executes instructions on the processor to determine if the detected movement of the at least one marker corresponds to a defined head movement of the surgeon. The visualization system further includes a surgical camera that moves with six degrees of freedom, and is controlled by the processor if the movement of the at least one marker corresponds to the defined head movement of the surgeon.

The visualization system and its methods of use may include the following additional features: i) the surgical camera may be a component of an NGENUITY® 3D Visualization System; ii) the defined head movement of the surgeon may be a quiet head movement, a deliberate head movement, an uncommon head movement, or any combination thereof; iii) the intelligent tracking system may include a noise detection system that includes a microphone and determines if the detected movement of the at least one marker corresponds to a quiet head movement of the surgeon; a motion thresholding system that determines if the detected movement of the at least one marker corresponds to a deliberate head movement of the surgeon, and a motion recognition system that determines if the detected movement of the at least one marker corresponds to an uncommon head movement of the surgeon; iv) a head movement that is not the defined head movement may be ignored by the head tracking control system; the defined head movement may be a displacement along an x-axis, a displacement along a y-axis, a pitch movement, or any combination thereof; v) the at least one marker may be an active infrared marker, a passive infrared marker, a fiducial marker, disposed in a cap, attached by adhesive, marked in pen, or any combination thereof.

The present disclosure further provides a method for controlling an ophthalmic surgical microscope by detecting a surgeon head movement using a head tracking control system; determining if the head movement is a quiet head movement; determining if the head movement is a deliberate head movement; determining if the head movement is an uncommon head movement; and if the head movement is a quiet head movement, a deliberate head movement, and an uncommon head movement, allowing the head tracking control system to control the ophthalmic surgical microscope.

The present disclosure further provides a method for controlling a visualization system by a surgeon by making a defined head movement; detecting the defined head movement using a surgeon head movement detection device; determining a corresponding movement of a surgical camera; and moving the surgical camera in response to the defined head movement. The defined head movement of the surgeon may be a quiet head movement, a deliberate head movement, an uncommon head movement, or any combination thereof. The surgical camera may move with six degrees of freedom. The surgical camera may be a component of an NGENUITY® 3D Visualization System.

Aspects of the head tracking control system and its methods of use may be combined with one another unless clearly mutually exclusive. In addition, the additional features of the head tracking control system and its associated methods described above may also be combined with one another unless clearly mutually exclusive.

BRIEF DESCRIPTION OF THE DRAWINGS

For a more complete understanding of the present disclosure and its features and advantages, reference is now made to the following description, taken in conjunction with the accompanying drawings, which are not to scale, in which like numerals refer to like features, and in which.

DETAILED DESCRIPTION

Figure 1:
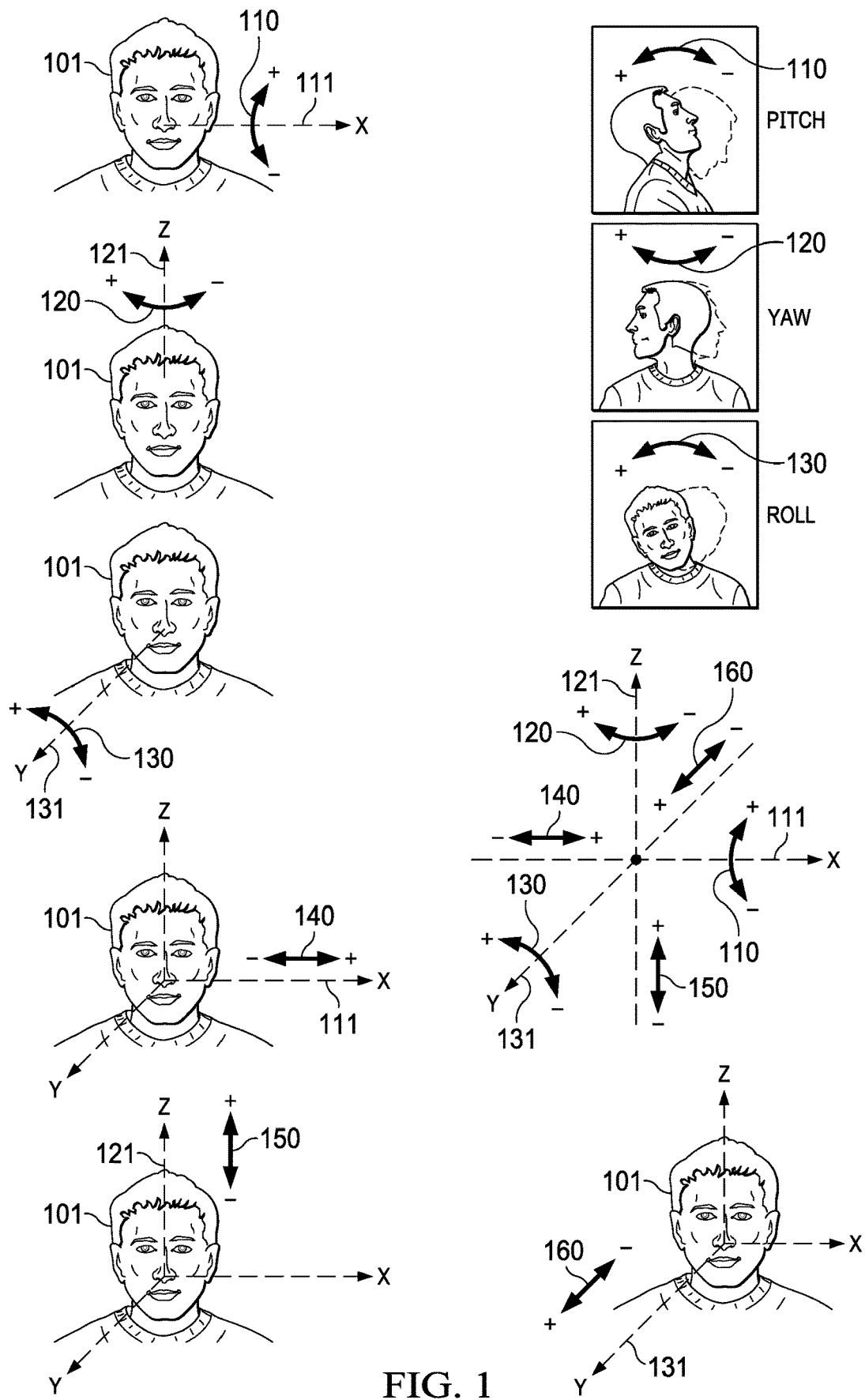
FIG. 1 is a schematic representation of the six degrees of freedom of surgeon head gestures and a frame of reference.

The present disclosure provides systems including head tracking control to improve visualization for ophthalmic surgery and associated methods.

Ophthalmic surgeons face unique challenges when visualizing the eye. During ophthalmic surgery it may be desirable for a surgeon to control a number of pieces of equipment, visualization systems, and surgical instruments. For example, in order to perform any of a variety of surgical procedures, a surgeon may desire to control the positioning or focus of a visualization system.

The present disclosure relates to surgeon head tracking control of a visualization system for ophthalmic surgery. During ophthalmic surgery, the surgeon is typically engaged with full attention and is using both hands to operate on the patient. Accordingly, the ability of the surgeon to provide continuous user input to, for example, position or focus a visualization system may be limited. Hand-operated selection controls for the visualization system (such as panel mounted controls, touch screen controls, focus rings, or any combination thereof) may be unsuitable or impossible for the surgeon to operate while performing surgery. A voice-operated selection control of the visualization system may also be unsuitable due to concerns about reliability, language customization, and a slow speed of voice recognition. Therefore, voice-operated controls may be particularly useful for selecting options involving a single command, rather than for continuously positioning or focusing a visualization system, which may involve rapid and repetitive user input.

A visualization system may include image acquisition positioning that is controlled by a foot pedal device. However, foot pedal control may result in inadvertent surgeon hand motion, which in turn may disrupt delicate surgical procedures. Furthermore, ophthalmic surgical systems typically include a first foot pedal for control of the ophthalmic surgical system, and optionally a second foot pedal to control a laser. As a surgeon only has two feet, it may be difficult to activate a third pedal for further control of positioning or focus of a visualization system. A head mounted display with head motion sensing may also be used to control a visualization system. This may be undesirable, however, as a head mounted display can cause nausea, vertigo, spatial disorientation, and fatigue. Use of a head mounted display also adds weight on the surgeon's head, which may cause cervical spine disease. Certain head tracking control systems for ophthalmic surgery also may not distinguish between head movements that are intended to control the visualization system and head movements that are instinctively made by the surgeon, for example head movements that are made while talking, and not intended to control the visualization system.

The head tracking control systems and methods of the present disclosure may provide for improved control of a visualization system for ophthalmic surgery. In particular, the head tracking control systems and methods of the present disclosure may provide for faster, safer, sterile, and more comfortable surgical procedures as compared to certain other control systems. The head tracking control systems and methods disclosed herein may provide hands-free control of a visualization system for ophthalmic surgery. This in turn may allow greater ease of use while providing for safer and more sterile surgical procedures. The head tracking control systems and methods disclosed herein may provide improved control of a visualization system as compared to certain other control systems by providing improved comfort for a surgeon. In particular, the head tracking control systems and methods disclosed herein may use a headband, hat or cap, as compared to certain other control systems that use a heavier head mounted display. This in turn may decrease nausea, vertigo, spatial disorientation, fatigue, and the weight on the head of the surgeon during surgery.

The head tracking control systems and methods disclosed herein may enable improved positioning and focus of a visualization system as compared to certain other control systems. In particular, the head tracking control systems and methods disclosed herein may allow improved control of a visualization system as compared to certain other control systems by limiting the types of head movement that may control a visualization system. For example, the head tracking control systems and methods of the current disclosure may only allow head movements of a surgeon that are defined head movements to control a visualization system. The head tracking control systems and methods of the present disclosure may also improve visualization for ophthalmic surgery as compared to certain other control systems by obeying the horizontal meridian. This may improve the ease of use and the responsiveness of the head tracking control system. The head tracking control systems and methods disclosed herein may allow improved control of a visualization system as compared to certain other control systems by providing a microphone to monitor the vocal gestures of the surgeon. By doing so, the systems and methods may allow the head tracking control system to ignore any head movement of the surgeon while they are, for example, speaking, coughing, or sneezing. The head tracking control systems and methods disclosed herein may allow improved control of a visualization system as compared to certain other control systems by ignoring head movements of the surgeon that are not deliberate, for example, fast or small head movements. The head tracking control systems and methods disclosed herein may allow improved control of a visualization system as compared to certain other control systems by ignoring common head movements, for example, a yaw head movement. A yaw head movement may be commonly associated with a surgeon speaking to other staff in the operating theatre.

The systems and methods disclosed herein may improve visualization for ophthalmic surgery by providing a head tracking control system that tracks the position of the head of surgeon using optical tracking, at least one 3-axis gyroscope sensor and at least one 3-axis accelerometer sensor, optical three-dimensional scanning, or any combination thereof. The systems and methods disclosed herein may include a headband, hat, or cap, or any combination thereof, positioned on the head of a surgeon. This may result in a reduced weight on the surgeon's head during surgery. The headband, hat, or cap may include at least one marker. The movement of the at least one marker may be detected by the head tracking control system, and in response to the movement instructions may be executed to control the visualization system.

Referring now to FIG. 1, head gestures used by surgeon 101 to control a visualization system may include six degrees of freedom on separate axes. Rotational degrees of freedom may include pitch 110, yaw 120 and roll 130. Translational degrees of freedom may include x 140, z 150 and y 160. Pitch 110, yaw 120 and roll 130 may all be zero when the surgeon has his or her head level and pointing directly forward. Pitch 110 may be rotational motion about lateral x-axis 111. Pitch 110 may be positive when surgeon 101 points his or her head upwards, and may be negative when surgeon 101 points his or her head downwards. Yaw 120 may be rotational motion about vertical z-axis 121. Yaw 120 may be positive when surgeon 101 turns his or her head to their right, and may be negative when surgeon 101 turns his or her head to their left. Roll 130 may be rotational motion about longitudinal y-axis 131. Roll 130 may be positive when surgeon 101 banks his or her head to their right, and may be negative when surgeon 101 banks his or her head to their left.

Translation x 140, z 150 and y 160 may be zero when the surgeon has his or her head in a neutral, un-extended position. Translation x 140 may be displacement along x-axis 111. Translation x 140 may be positive when surgeon 101 displaces his or her head to their left, and may be negative when surgeon 101 displaces his or her head to their right. Translation z 150 may be displacement along z-axis 121. Translation z 150 may be positive when surgeon 101 displaces his or her head upwards, and may be negative when surgeon 101 displaces his or her head downwards. Translation y 160 may be displacement along y-axis 131. Translation y 160 may be positive when surgeon 101 displaces his or her head forward, and may be negative when surgeon 101 displaces his or her head backward.

Figure 2:
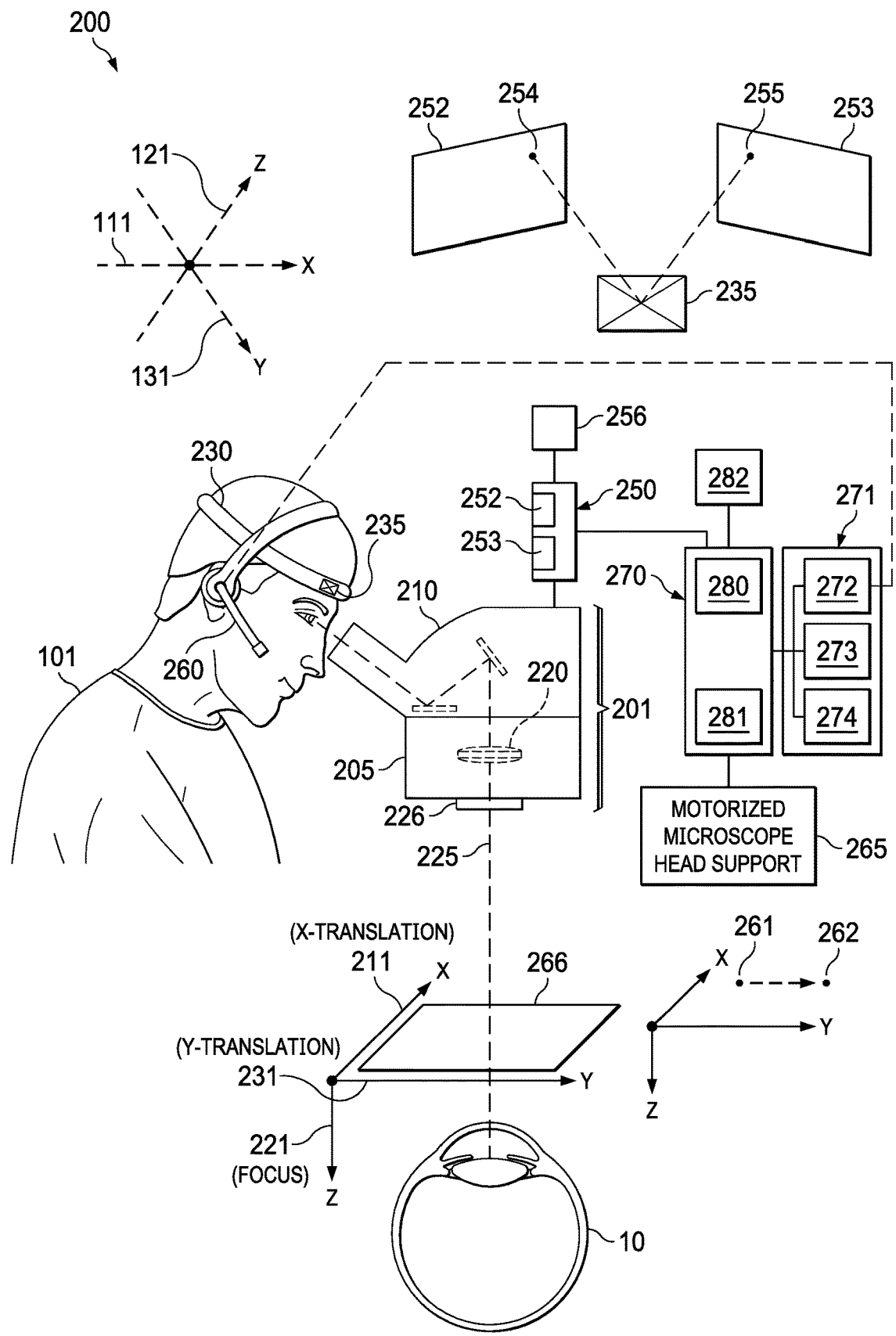
FIG. 2 is a schematic representation of a head tracking control system, including an ophthalmic surgical microscope, a headband, an infrared camera, an intelligent tracking system, and a motorized microscope head support.

Referring now to FIG. 2, head tracking control system 200 may include ophthalmic surgical microscope 201, headband 230, infrared camera 250, and motorized microscope head support 265. Ophthalmic surgical microscope 201 may include microscope body 205, binoculars 210, and objective 220. Objective 220 may be placed in an optical path 225 (dotted line) and may represent a selectable objective to provide a desired magnification or field of view of the fundus of eye 10. Objective 220 may be moved closer or away from eye 10 to change the focus of ophthalmic surgical microscope 201. Ophthalmic surgical microscope 201 may include illumination source 226. Illumination source 226 may be an endoilluminator (not shown). Alternatively, illumination source 226 may be provided by an ophthalmic surgical microscope, such as ophthalmic surgical microscope 201, or another ophthalmic visualization system, such as the NGENUITY® 3D Visualization System (Novartis AG Corp., Switzerland).

Binoculars 210 may be used in conjunction with microscope body 205 and may be positioned in optical path 225. Optical path 225 may extend through binoculars 210 to the eye of surgeon 101. Portions of eye 10 suitable for viewing using ophthalmic surgical microscope 201 may include the retina, macula (for example, the foveola, fovea centralis, para fovea, and perifovea), cornea, iris, lens, lens capsule, optic disc (for example, the optic cup), one of more layers of the retina, vitreous, vitreous body, retinal pigment epithelium, choroid, or any portion in which a surgical instrument is also viewed.

Ophthalmic surgical microscope 201 may further include various other electronic and mechanical components in different implementations. Accordingly, while the particular optical design discussed with reference to FIG. 2 is specific to an ophthalmic visualization system that includes ophthalmic surgical microscope 201, one skilled in the art will appreciate that alternative optical arrangements to support other ophthalmic visualization systems are within the scope of the disclosure.

During surgery, surgeon 101 may use ophthalmic surgical microscope 201 to view at least a portion of eye 10. Eye 10 may be illuminated by illumination source 226. Ophthalmic surgical microscope 201 may have an exemplary field of view that includes XY plane 266. XY plane 266 may be formed by microscope movement x-axis 211 and microscope movement y-axis 231. XY plane 266 may be a horizontal plane that is about parallel to the floor of the operating room. XY plane 266 may be a plane that is about horizontal above eye 10 during surgery. Objective 220 may be moved closer or away from eye 10 along focus z-axis 221 to change the focus of ophthalmic surgical microscope 201. In another example, the focus of ophthalmic surgical microscope 201 may be changed opto-mechanically by moving optical elements called cells, or the entire microscope closer or away from eye 10.

Head tracking control system 200 may track the position of the head of surgeon 101 using optical tracking. In particular, head tracking control system 200 may track the position of the head of surgeon 101 using infrared camera 250 and headband 230. Infrared camera 250 may be a camera that detects infrared light, which may be light having a wavelength in the range of 0.7-1000 microns. Headband 230 may be positioned on the head of surgeon 101. Headband 230 may alternatively be a hat or cap. Headband 230 may include at least one marker 235. During surgery, the position of the at least one marker 235 may be tracked using infrared camera 250.

Marker 235 may be an active infrared marker. An active infrared marker may include an infrared light emitting element, and may include at least one light emitting diode (LED). In one example, marker 235 may include six active beacons. The inclusion of six active beacons may allow marker 235 to be tracked as a rigid body with six degrees of freedom. In another example, marker 235 may include six LEDs. The LEDs may be flashed in a time synchronous controlled sequence. In another example, marker 235 may include at least one passive infrared marker, and may include at least one passive reflective marker. Marker 235 may include six passive infrared markers. The inclusion of six passive markers may allow marker 235 to be tracked as a rigid body with six degrees of freedom. Marker 235 may function as a fiducial. Marker 235 may function as a fiducial in a captured image, in real space, or a combination thereof. Marker 235 may be disposed in a cap, attached by adhesive, marked in pen, marked by any other means, or any combination thereof. Marker 235 may be placed in any orientation necessary such that its position may be tracked in six degrees of freedom.

Infrared camera 250 may be mounted on the top of ophthalmic surgical microscope 201. Infrared camera 250 may alternatively be positioned in any suitable location to track the at least one marker 235. For example, infrared camera 250 may be positioned in the range of from about 2 feet to about 6 feet from marker 235. Infrared camera 250 may detect reflected infrared light, may detect emitted infrared light, or a combination thereof. Infrared camera 250 may have a field of view that is wide enough to include the at least one marker 235. Infrared camera 250 may include at least infrared sensors 252 and 253. Infrared sensors 252 and 253 may be photodetectors that detect infrared light. Infrared sensors 252 and 253 may be two paired area array infrared sensors. Infrared sensors 252 and 253 may be active infrared image sensors, time-of-flight range sensors, infrared sensitive CMOS sensors, infrared sensitive CCD sensors, or any combination thereof. In an alternative example, infrared camera 250 may be substituted for three line scan infrared cameras. Infrared camera 250 may use infrared sensors 252 and 253 to detect infrared light reflected off the at least one marker 235. Alternatively, infrared camera 250 may use infrared sensors 252 and 253 to detect infrared light emitted by the at least one marker 235. Infrared camera 250 may include active infrared illuminator 256, which may emit infrared light in the thermal part of the infrared spectrum. Infrared camera 250 may use infrared sensors 252 and 253 to detect infrared light emitted by active infrared illuminator 256 and reflected off the at least one marker 235.

Head tracking control system 200 may include image processing system 270. Digital images captured by infrared sensors 252 and 253 may be processed by image processing system 270. Image processing system 270 may include processor 280. Infrared sensors 252 and 253 may detect infrared light reflected off the at least one marker 235 and send a signal corresponding to the detected light to processor 280.

Processor 280 may include, for example, a field-programmable gate array (FPGA), a microprocessor, a microcontroller, a digital signal processor (DSP), a graphics processing unit (GPU), an application specific integrated circuit (ASIC), or any other digital or analog circuitry configured to interpret and/or execute program instructions and/or process data.

Processor 280 may include any physical device able to store and/or execute instructions. Processor 280 may execute processor instructions to implement at least a portion of one or more systems, one or more flow charts, one or more processes, and/or one or more methods described herein. For example, processor 280 may execute instructions to track the position of the head of surgeon 101. Processor 280 may be configured to receive instructions from memory medium 281. In one example, processor 280 may include memory medium 281. In another example, memory medium 281 may be external to processor 280. Memory medium 281 may store the instructions. The instructions stored by memory medium 281 may be executable by processor 280 and may be configured, coded, and/or encoded with instructions in accordance with at least a portion of one or more systems, one or more flowcharts, one or more methods, and/or one or more processes described herein.

A FPGA may be may be configured, coded, and/or encoded to implement at least a portion of one or more systems, one or more flow charts, one or more processes, and/or one or more methods described herein. For example, the FPGA may be configured, coded, and/or encoded to track the position of the head of surgeon 101. An ASIC may be may be configured to implement at least a portion of one or more systems, one or more flow charts, one or more processes, and/or one or more methods described herein. For example, the ASIC may be configured, coded, and/or encoded to track the position of the head of surgeon 101. A DSP may be may be configured, coded, and/or encoded to implement at least a portion of one or more systems, one or more flow charts, one or more processes, and/or one or more methods described herein. For example, the DSP may be configured, coded, and/or encoded to track the position of the head of surgeon 101.

A single device may include processor 280 and image processing system 270, or processor 280 may be separate from image processing system 270. In one example, a single computer system may include processor 280 and image processing system 270. In another example, a device may include integrated circuits that may include processor 280 and image processing system 270. Alternatively, processor 280 and image processing system 270 may be incorporated into a surgical console.

Processor 280 may interpret and/or execute program instructions and/or process data stored in memory medium 281. Memory medium 281 may be configured in part or whole as application memory, system memory, or both. Memory medium 281 may include any system, device, or apparatus configured to hold and/or house one or more memory devices. Each memory device may include any system, any module or any apparatus configured to retain program instructions and/or data for a period of time (e.g., computer-readable media). One or more servers, electronic devices, or other machines described may include one or more similar such processors or memories that may store and execute program instructions for carrying out the functionality of the associated machine.

Infrared sensors 252 and 253 may detect infrared light reflected off the at least one marker 235 at detection points 254 and 255, respectively, and send a signal corresponding to detection points 254 and 255 to processor 280. The relative position of detection points 254 and 255 on each of infrared sensors 252 and 253, respectively, may define the three-dimensional location of the at least one marker 235. Infrared sensors 252 and 253 may be placed in any relative orientation suitable to define the three-dimensional location of the at least one marker 235.

The position of marker 235 may be tracked using infrared camera 250 in real time. As used herein, "real time" may refer to the updating of information at the same rate as data is received. In the context of the head tracking control systems and methods of the present disclosure, "real time" may mean that image data is acquired, processed, and transmitted from a photosensor at a high enough data rate and a low enough delay that when the data is displayed, objects more smoothly without user-noticeable judder or latency. For example, this may occur when new images are acquired, processed, and transmitted at a rate of at least 30 frames per second and displayed at about 60 frames per second, and where the combined processing of the signal has less than about a $\frac{1}{30}^{th}$ second of delay.

Infrared camera 250 may detect infrared light reflected off the at least one marker 235 using infrared sensors 252 and 253 and send a signal corresponding to the detected light to processor 280. Infrared camera 250 may further execute instructions on processor 280 to detect a movement of the at least one marker 235. The movement of the at least one marker 235 may be analyzed by intelligent tracking system 271. The movement of marker 235 detected by infrared camera 250 may correspond to a head movement of surgeon 101 that is pitch 110, yaw 120, roll 130, x 140, z 150, y 160, or any combination thereof. The head movement of surgeon 101 may be described by Cartesian co-ordinates corresponding to x-axis 111, z-axis 121 and y-axis 131.

Intelligent tracking system 271 may execute instructions on processor 280 to determine if the movement of the at least one marker 235 corresponds to a defined head movement of surgeon 101. Intelligent tracking system 271 may include noise detection system 272, motion thresholding system 273, and motion recognition system 274. Intelligent tracking system 271 may allow head tracking control system 200 to control ophthalmic surgical microscope 201 when surgeon 101 makes a defined head movement. A defined head movement may include a quiet head movement, a deliberate head movement, an uncommon head movement, or any combination thereof. A defined head movement may correspond to a characteristic movement of marker 235 detected by infrared camera 250.

A quiet head movement may include a head movement that is not accompanied by a noise from surgeon 101. The noise may include speech, a sneeze, a cough, a sigh, or any combination thereof. Speech by the surgeon may include communicating with others in the operating room. Quiet head movements may be detected by noise detection system 272. Noise detection system 272 may be communicatively coupled to microphone 260. Microphone 260 may be worn by surgeon 101. Microphone 260 may be a wireless microphone. Microphone 260 may be a head mounted microphone. A head movement may be a quiet head movement if little or no signal is detected from microphone 260 at about the same time as a movement of marker 235 is detected by infrared camera 250. Noise detection system 272 may determine if a head movement is a quiet head movement and send a signal corresponding to the determination to processor 280. Processor 280 may execute instructions to control ophthalmic surgical microscope 201 in response to the quiet head movement.

A deliberate head movement may include a head movement that is made with purpose by surgeon 101, for example, a head movement that is not an instinctive head movement. A deliberate head movement may include a head movement that is slower than an instinctive head movement, a head movement that is larger in magnitude than an instinctive head movement, a head movement that is smoother in motion than an instinctive head movement, or any combination thereof. A deliberate head movement may be a head movement that is slower than a head movement that occurs at 2 Hz. Alternatively, a deliberate head movement may be a head movement that is slower than a head movement that occurs at 4 Hz. A deliberate head movement may be a head movement that is larger in magnitude than a head movement of 1 mm, as measured by movement of a particular point on the surgeon's head through three-dimensional space. Alternatively, a deliberate head movement may be a head movement that is in the range of from about 1 mm to about 16 mm, as measured by movement of a particular point on the surgeon's head through three-dimensional space. A deliberate head movement may be a head movement that is smoother in motion than a head movement that accelerates the head faster than 1 m/s$^2$. A deliberate head movement may be a head movement that is smoother in motion than a head movement that accelerates the head faster than 2 m/s$^2$. Deliberate head movements may be detected by motion thresholding system 273. A head movement may be a deliberate head movement if the movement of marker 235 detected by infrared camera 250 is slow, large in magnitude, smooth, or any combination thereof. Alternatively, a head movement may be a deliberate head movement if the movement of marker 235 detected by infrared camera 250 is slow, large in magnitude, and smooth. Motion thresholding system 273 may determine if a head movement is a deliberate head movement and send a signal corresponding to the determination to processor 280. Processor 280 may execute instructions to control ophthalmic surgical microscope 201 in response to the deliberate head movement.

An uncommon head movement may include a head movement that is not commonly made by a surgeon during surgery. For example, an uncommon head movement may include a translation x 140 or y 160. Common surgeon movements that occur frequently during surgery may include yaw 120, for example, to address other staff in the operating room. Uncommon head movements may be detected by motion recognition system 274. A head movement may be an uncommon head movement if the movement of marker 235 detected by infrared camera 250 corresponds to a head movement that is not commonly made by a surgeon during surgery. Motion recognition system 274 may determine if a head movement is an uncommon head movement and send a signal corresponding to the determination to processor 280. Processor 280 may execute instructions to control ophthalmic surgical microscope 201 in response to the uncommon head movement.

Intelligent tracking system 271 may allow head tracking control system 200 to control ophthalmic surgical microscope 201 if surgeon 101 makes a defined head movement that is a quiet head movement, a deliberate head movement, and an uncommon head movement. Alternatively, intelligent tracking system 271 may allow head tracking control system 200 to control ophthalmic surgical microscope 201 if surgeon 101 makes a defined head movement that is a quiet head movement, a deliberate head movement, an uncommon head movement, or any combination thereof. A surgeon head movement that is not a defined head movement may be ignored by head tracking control system 200.

Ophthalmic surgical microscope 201 may execute instructions on processor 280 in response to a defined head movement of surgeon 101. For example, processor 280 may execute instructions to move motorized microscope head support 265 in response to the defined head movement of surgeon 101. The movement of motorized microscope head support 265 may be described by a two-dimensional Cartesian co-ordinate system of microscope movement x-axis 211 and microscope movement y-axis 231.

For example, a movement of the at least one marker 235 that corresponds to a defined head movement of x 140 by surgeon 101 may be detected by infrared camera 250 and a signal corresponding to the detected movement may be sent to processor 280. Processor 280 may execute instructions to move motorized microscope head support along microscope movement x-axis 211. This may change the field of view that includes XY plane 266 observed by surgeon 101 along microscope movement x-axis 211. Similarly, a movement of the at least one marker 235 that corresponds to a defined head movement of y 160 by surgeon 101 may be detected by infrared camera 250 and a signal corresponding to the detected movement may be sent to processor 280. Processor 280 may execute instructions to move motorized microscope head support along microscope movement y-axis 231. This may change the field of view that includes XY plane 266 observed by surgeon 101 along microscope movement y-axis 231.

Alternatively, processor 280 may execute other instructions to control ophthalmic surgical microscope 201 in response to a defined head movement of surgeon 101. For example, a movement of the at least one marker 235 that corresponds to a defined head movement that includes z 150 and pitch 110 by surgeon 101 may be detected and a signal corresponding to the detected movement may be sent to processor 280. Processor 280 may execute instructions to change the focus of ophthalmic surgical microscope 201 by moving objective 220. Objective 220 may be moved along focus z-axis 221. If z 150 and pitch 110 are positive, processor 280 may execute instructions to move objective 220 away from eye 10 along focus z-axis 221 within surgical microscope 201. If z 150 and pitch 110 are negative, processor 280 may execute instructions to move objective 220 closer to eye 10 along focus z-axis 221. Processor 280 may execute instructions to control ophthalmic surgical microscope 201 in any manner useful for ophthalmic surgery in response to any appropriate defined head movement of surgeon 101. Such instructions may be unique and programmable to accommodate the preference of individual ophthalmic surgeons.

The instructions executed by processor 280 to control ophthalmic surgical microscope 210 may be movement instructions. Movement instructions may have a parameter of velocity, which may be measured, for example, in units such as mm/second or μm/second. The velocity of the movement instructions may be fixed or variable. The velocity of the movement instructions may vary according to the position of the corresponding movement. For example, the velocity of movement instructions to move motorized microscope head support 265 in response to the defined head movement of surgeon 101 may vary according to the position of motorized microscope head support 265. A movement of the at least one marker 235 that corresponds to a defined head movement of y 160 by surgeon 101 may be detected by infrared camera 250 and a signal corresponding to the detected movement may be sent to processor 280. Processor 280 may execute movement instructions to move motorized microscope head support along microscope movement y-axis 231. Motorized microscope head support 265 may move from start point 261 to end point 262. As motorized microscope head support 265 moves away from start point 261, the velocity of the movement instructions may increase with increasing distance from start point 261. This increase may continue until motorized microscope head support 265 reaches a point equidistant between start point 261 and end point 262. The velocity of the movement instructions may then decrease with decreasing distance of motorized microscope head support 265 to end point 262. Accordingly, the movement instructions may be configured to result in a slow ramping up and ramping down of the velocity of the movement of motorized microscope head support 265. The movement instructions may also be configured to result in any velocity of movement of a component of ophthalmic surgical microscope 210 that improves visualization for ophthalmic surgery.

Head tracking control system 200 may include control device 282. Control device 282 may adjust, for example, the settings of intelligent tracking system 271, the sensitivity of microphone 260, the velocity of movement instructions executed by processor 280, any other surgeon specific settings of head tracking control system 200, or any combination thereof.

Figure 3:
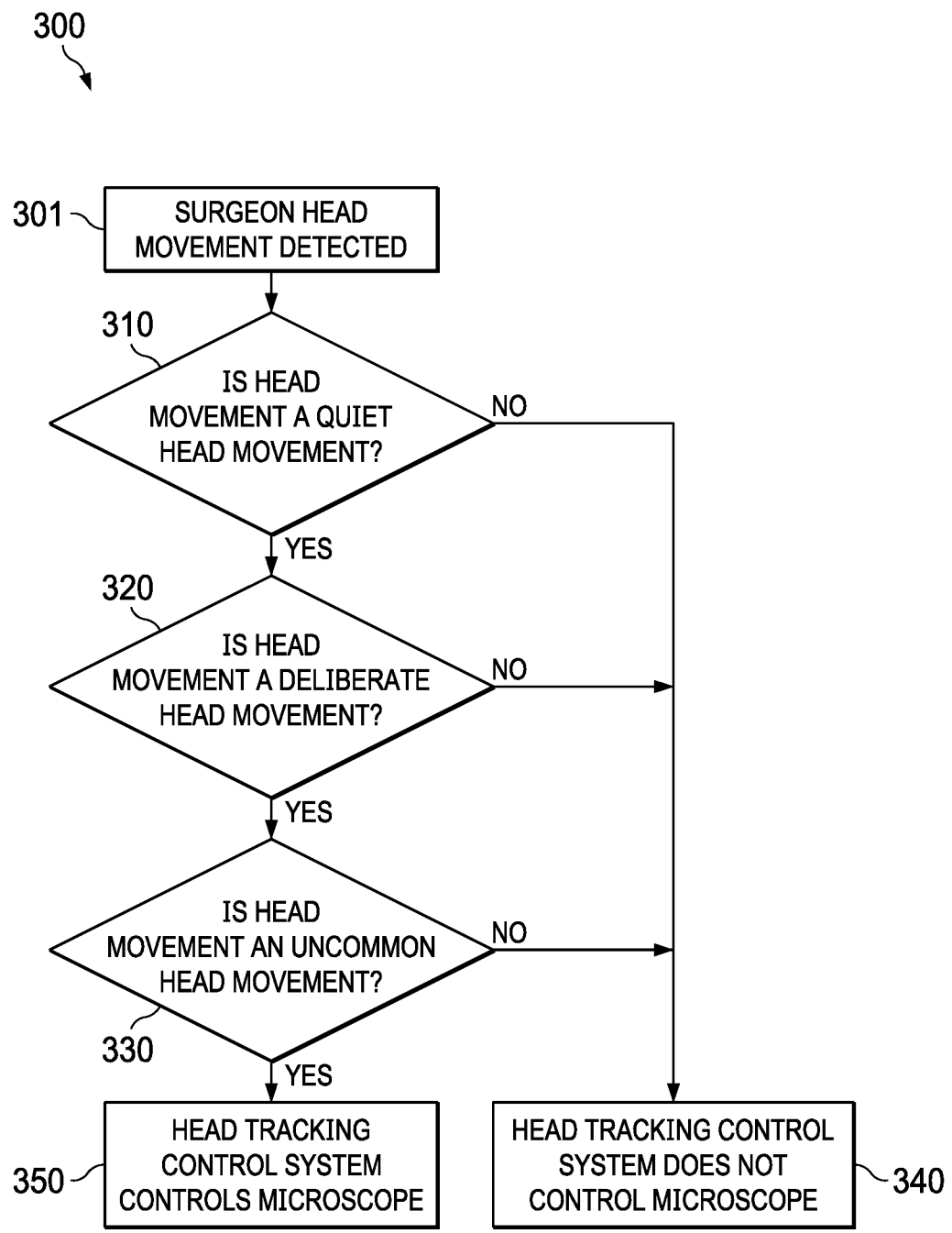
FIG. 3 is a schematic representation of a process flow for controlling an ophthalmic surgical microscope using a head tracking control system.

FIG. 3 depicts a process flow 300 for controlling an ophthalmic surgical microscope using a head tracking control system. Process flow 300 may include detecting a surgeon head movement in step 301. The head movement may be detected by an infrared camera such as infrared camera 250. Process flow 300 may further include determining if the head movement is a quiet head movement in step 310. A noise detection system, such as noise detection system 272, may detect if a head movement is a quiet head movement. If the head movement is not a quiet head movement, in step 340 the head tracking control system, such as head tracking control system 200, may not control the ophthalmic surgical microscope, such as ophthalmic surgical microscope 201. If the head movement is a quiet head movement, process flow 300 may include determining if the head movement is a deliberate head movement in step 320. A motion thresholding system, such as motion thresholding system 273, may detect if a head movement is a deliberate head movement. If the head movement is not a deliberate head movement, in step 340 the head tracking control system may not control the ophthalmic surgical microscope. If the head movement is a deliberate head movement, process flow 300 may include determining if the head movement is an uncommon head movement in step 330. A motion recognition system, such as motion recognition system 274, may detect if a head movement is an uncommon head movement. If the head movement is not an uncommon head movement, in step 340 the head tracking control system may not control the ophthalmic surgical microscope. If the head movement is an uncommon head movement, process flow 300 may include allowing the head tracking control system, such as head tracking control system 200, to control the ophthalmic surgical microscope.

In process flow 300, a surgeon head movement that is a quiet head movement, a deliberate head movement, and an uncommon head movement may allow the head tracking control system to control the ophthalmic surgical microscope. Alternatively, a surgeon head movement that is a quiet head movement, a deliberate head movement, an uncommon head movement, or any combination thereof, may allow a head tracking control system to control the ophthalmic surgical microscope.

Figure 4:
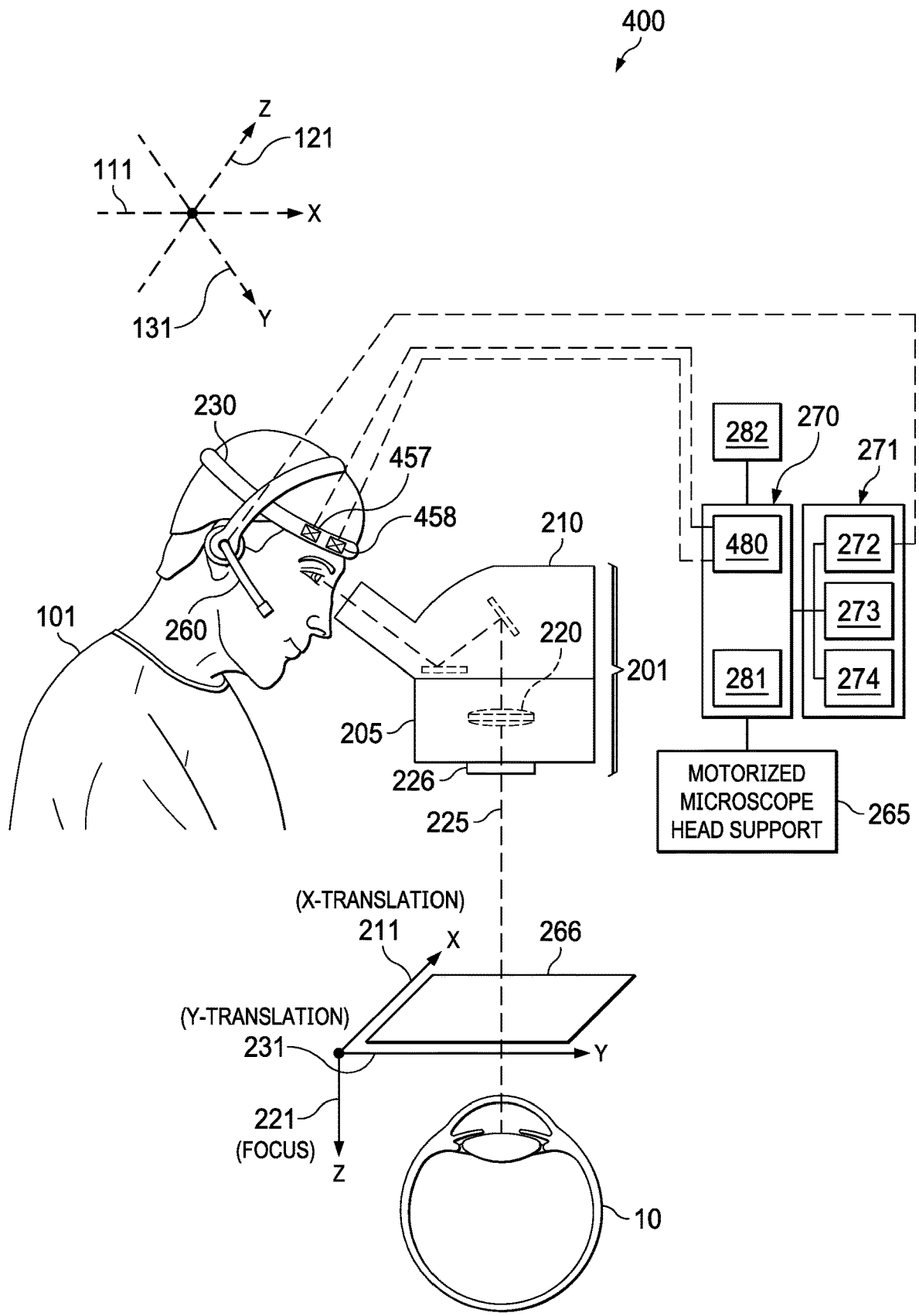
FIG. 4 is a schematic representation of a head tracking control system, including an ophthalmic surgical microscope, a headband, a 3-axis gyroscope and a 3-axis accelerometer, an intelligent tracking system, and a motorized microscope head support.

Referring now to FIG. 4, head tracking control system 400 may include ophthalmic surgical microscope 201, headband 430, 3-axis gyroscope 457, 3-axis accelerometer 458, and motorized microscope head support 265.

Head tracking control system 400 may track the head movement of surgeon 101 using at least one gyroscope sensor and at least one accelerometer sensor. For example, head tracking control system 400 may include 3-axis gyroscope 457 and 3-axis accelerometer 458 mounted on headband 430. Headband 430 may be positioned on the head of surgeon 101. 3-axis gyroscope 457 and 3-axis accelerometer 458 may be wirelessly communicatively coupled to processor 480. In another example, head tracking control system 400 may include a vibrating structure gyroscope sensor. Head tracking control system 400 may include a gyroscope sensor contained on a single chip. Head tracking control system 400 may include an accelerometer sensor contained on a single chip. Headband 430 may alternatively be a hat or cap.

3-axis gyroscope 457 may be a 3-axis gyroscope sensor that may detect the angular velocity of the head of surgeon 101 wearing headband 430. 3-axis gyroscope 457 may also detect the rotational motion pitch 110, yaw 120, roll 130 of the head of surgeon 101. 3-axis accelerometer 458 may be a 3-axis accelerometer sensor that may detect the acceleration of the head of surgeon 101 wearing headband 430. 3-axis accelerometer 458 may also detect translation x 140, z 150, y 160 of the head of surgeon 101.

During surgery, 3-axis gyroscope 457 and 3-axis accelerometer 458 may detect the head movement of surgeon 101 and send a signal corresponding to the detected movement to processor 480. The head movement of surgeon 101 may be analyzed by intelligent tracking system 271. The head movement of surgeon 101 detected by 3-axis gyroscope 457 and 3-axis accelerometer 458 may correspond to a head movement that is pitch 110, yaw 120, roll 130, x 140, z 150, y 160, or any combination thereof. The head movement of surgeon 101 may be described by Cartesian co-ordinates corresponding to x-axis 111, z-axis 121 and y-axis 131. The head movement of surgeon 101 may be tracked using 3-axis gyroscope 457 and 3-axis accelerometer 458 in real time.

Intelligent tracking system 271 may execute instructions on processor 480 to determine if the head movement of surgeon 101 corresponds to a defined head movement. Intelligent tracking system 271 may include noise detection system 272, motion thresholding system 273, and motion recognition system 274. Intelligent tracking system 271 may allow head tracking control system 400 to control ophthalmic surgical microscope 201 when surgeon 101 makes a defined head movement. A defined head movement may include a quiet head movement, a deliberate head movement, an uncommon head movement, or any combination thereof. A defined head movement may correspond to a characteristic head movement of surgeon 101 as detected by 3-axis gyroscope 457 and 3-axis accelerometer 458.

Intelligent tracking system 271 may allow head tracking control system 400 to control ophthalmic surgical microscope 201 if surgeon 101 makes a defined head movement that is a quiet head movement, a deliberate head movement, and an uncommon head movement. Alternatively, intelligent tracking system 271 may allow head tracking control system 400 to control ophthalmic surgical microscope 201 if surgeon 101 makes a defined head movement that is a quiet head movement, a deliberate head movement, an uncommon head movement, or any combination thereof. Accordingly, a surgeon head movement that is not a defined head movement may be ignored by head tracking control system 400.

Ophthalmic surgical microscope 201 may execute instructions on processor 480 in response to a defined head movement of surgeon 101. For example, processor 480 may execute instructions to move motorized microscope head support 265 in response to the defined head movement of surgeon 101. The movement of motorized microscope head support 265 may be described by a two-dimensional Cartesian co-ordinate system corresponding to microscope movement x-axis 211 and microscope movement y-axis 231. Alternatively, processor 480 may execute other instructions to control ophthalmic surgical microscope 201 in response to a defined head movement of surgeon 101.

Figure 5:
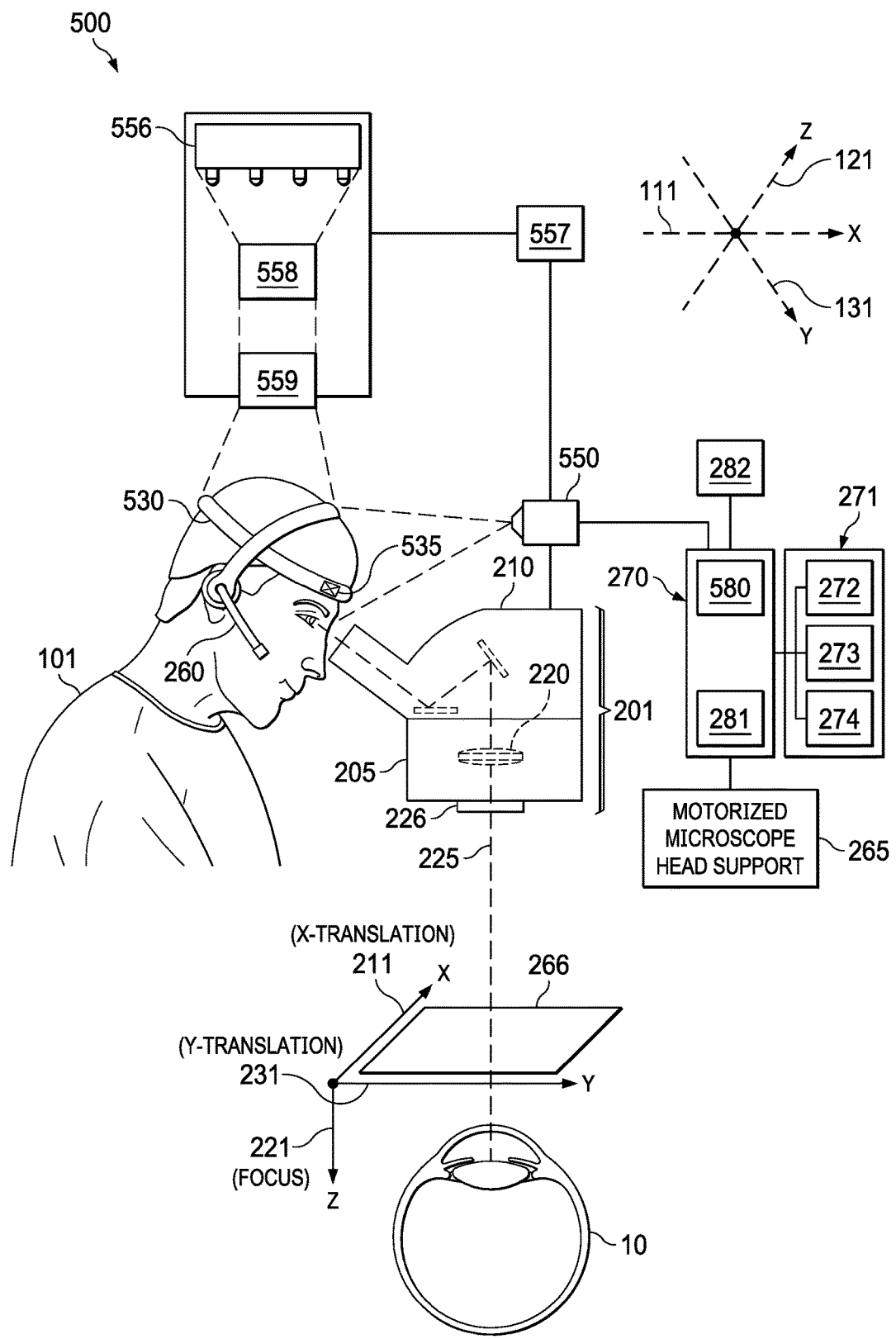
FIG. 5 is a schematic representation of a head tracking control system, including an ophthalmic surgical microscope, a headband, a three-dimensional scanning camera, a light emitting diode (LED) driver, a digital light processing controller chip, a digital micromirror device, a lens, an intelligent tracking system, and a motorized microscope head support.

Referring now to FIG. 5, head tracking control system 500 may include ophthalmic surgical microscope 201, headband 530, three-dimensional scanning camera 550, LED driver 556, digital light processing controller chip 557, digital micromirror device 558, lens 559, and motorized microscope head support 265.

Head tracking control system 500 may track the head movement of surgeon 101 using optical three-dimensional scanning to provide a digitized three-dimensional scan of the head of surgeon 101. Three-dimensional scanning may be performed using structured light, which may be provided by digital micromirror device 558. Three-dimensional scanning using structured light is an optical method where a series of patterns may be projected upon the head of surgeon 101. Three-dimensional scanning camera 550 may detect distortions in the patterns of structured light reflected off the head of surgeon 101. Image processing and triangulation algorithms, which may be performed by image processing system 270, may convert these distortions into a three-dimensional point cloud. The point cloud may be used to determine a head movement of surgeon 101.

Digital light processing controller chip 557 may control an array of reflective aluminum mirrors disposed on digital micromirror device 558. LED driver 556 may emit near-infrared light (for example, wavelengths in the range of from 700 nm-2500 nm). In an alternative configuration, LED driver 556 may be substituted for a lamp or laser. Digital micromirror device 558 may modulate the amplitude, direction, phase, or any combination thereof, of incoming light emitted by LED driver 556. Light emitted by LED driver 556 and modulated by digital micromirror device 558 may pass through lens 559.

Head tracking control system 500 may include headband 530. Headband 530 may be positioned on the head of surgeon 101. Headband 530 may alternatively be a hat or cap. Headband 530 may include at least one marker 535. Marker 535 may include six passive infrared markers. The inclusion of six passive markers may allow marker 535 to be tracked as a rigid body with six degrees of freedom. During surgery, the position of the at least one marker 535 may be tracked using three-dimensional scanning camera 550 using optical three-dimensional scanning. Marker 535 may function as a fiducial. Marker 535 may function as a fiducial in a captured image. Marker 535 may also function as a fiducial in real space. Marker 535 may be disposed in a cap, attached by adhesive, marked in pen, marked by any other means, or any combination thereof. Marker 535 may be placed in any orientation necessary such that its position may be tracked in six degrees of freedom.

Three-dimensional scanning camera 550 may detect structured light reflected off the at least one marker 535 and send a signal corresponding to the detected light to processor 580. Three-dimensional scanning camera 550 may further execute instructions on processor 280 to detect a movement of the at least one marker 535. The movement of the at least one marker 535 may be analyzed by intelligent tracking system 271. The movement of marker 535 detected by three-dimensional scanning camera 550 may correspond to a head movement of surgeon 101 that is pitch 110, yaw 120, roll 130, x 140, z 150, y 160, or any combination thereof. The head movement of surgeon 101 may be described by Cartesian co-ordinates corresponding to x-axis 111, z-axis 121 and y-axis 131. The head movement of surgeon 101 may be tracked using three-dimensional scanning camera 550 in real time. In another example, three-dimensional scanning camera 550 may be a LIPSedge™ AE400 stereo camera (LIPS Corp., Taiwan).

Intelligent tracking system 271 may execute instructions on processor 580 to determine if the movement of the at least one marker 535 corresponds to a defined head movement of surgeon 101. Intelligent tracking system 271 may include noise detection system 272, motion thresholding system 273, and motion recognition system 274. Intelligent tracking system 271 may allow head tracking control system 500 to control ophthalmic surgical microscope 201 when surgeon 101 makes a defined head movement. A defined head movement may include a quiet head movement, a deliberate head movement, an uncommon head movement, or any combination thereof. A defined head movement may correspond to a characteristic movement of marker 535 detected by three-dimensional scanning camera 550.

Intelligent tracking system 271 may allow head tracking control system 500 to control ophthalmic surgical microscope 201 if surgeon 101 makes a defined head movement that is a quiet head movement, a deliberate head movement, and an uncommon head movement. Alternatively, intelligent tracking system 271 may allow head tracking control system 500 to control ophthalmic surgical microscope 201 if surgeon 101 makes a defined head movement that is a quiet head movement, a deliberate head movement, an uncommon head movement, or any combination thereof. Accordingly, a surgeon head movement that is not a defined head movement may be ignored by head tracking control system 500.

Ophthalmic surgical microscope 201 may execute instructions on processor 580 in response to a defined head movement of surgeon 101. For example, processor 580 may execute instructions to move motorized microscope head support 265 in response to the defined head movement of surgeon 101. The movement of motorized microscope head support 265 may be described by a two-dimensional Cartesian co-ordinate system corresponding to microscope movement x-axis 211 and microscope movement y-axis 231. Alternatively, processor 580 may execute other instructions to control ophthalmic surgical microscope 201 in response to a defined head movement of surgeon 101.

Figure 6:
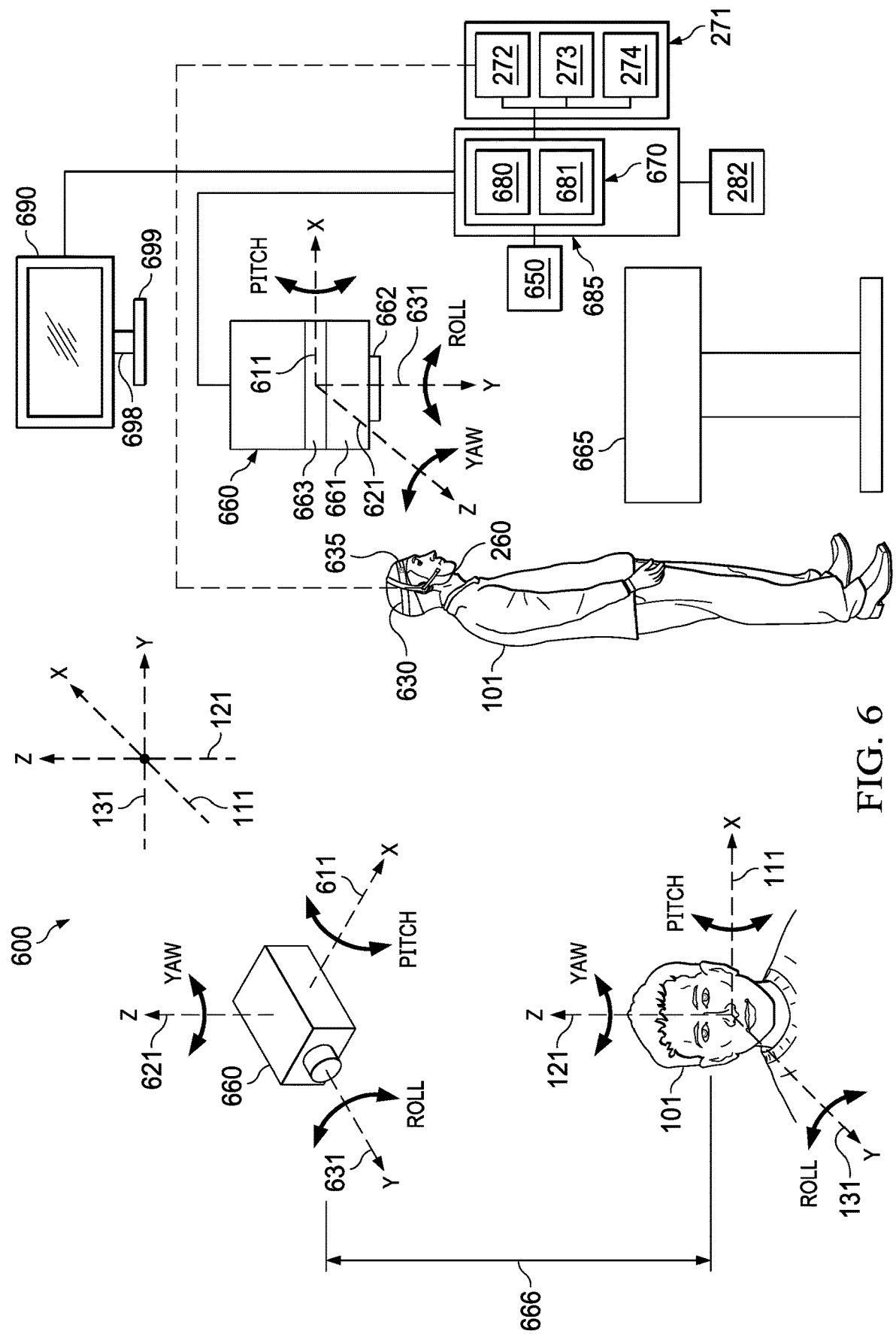
FIG. 6 is a schematic representation of a head tracking control system as a component of an NGENUITY® 3D Visualization System (Novartis AG Corp., Switzerland)

Head tracking control system 200, head tracking control system 400, or head tracking control system 500 may be used, at least in part, as a component of the NGENUITY® 3D Visualization System (Novartis AG Corp., Switzerland) in visualization system 600, as depicted in FIG. 6. Visualization system 600 may include headband 630, surgeon head movement detection device 650, intelligent tracking system 271, surgical camera 660, patient table 665, surgical camera system 685, and display 690. Surgeon head movement detection device 650 may be a device such as infrared camera 250, 3-axis gyroscope 457 and 3-axis accelerometer 458, three-dimensional scanning camera 550, or any combination thereof.

Headband 630 may be positioned on the head of surgeon 101. Headband 630 may alternatively be a hat or cap. Headband 630 may include at least one marker 635. During surgery, the position of the at least one marker 635 may be tracked using surgeon head movement detection device 650. Marker 635 may be an active infrared marker. An active infrared marker may include an infrared light emitting element, and may include at least one light emitting diode (LED). In one example, marker 635 may include six active beacons. The inclusion of six active beacons may allow marker 635 to be tracked as a rigid body with six degrees of freedom. In another example, marker 635 may include six LEDs. The LEDs may be flashed in a time synchronous controlled sequence.

Marker 635 may be a passive reflective marker. Marker 635 may include six passive infrared markers. The inclusion of six passive markers may allow marker 635 to be tracked as a rigid body with six degrees of freedom. Marker 635 may function as a fiducial. Marker 635 may function as a fiducial in a captured image. Marker 635 may also function as a fiducial in real space. If at least part of head tracking control system 400 is included as a component of visualization system 600, headband 630 may include a 3-axis gyroscope and a 3-axis accelerometer, such as 3-axis gyroscope 457 and 3-axis accelerometer 458, instead of marker 635 (not shown).

Surgical camera 660 may be positioned above patient table 665. Surgical camera 660 may be a digital camera, an HDR camera, a 3D camera, a surgical camera, or any combination thereof. Surgical camera 660 may move with six degrees of freedom. Surgical camera 660 may also utilize optomechanical focus system 661, zoom system 662, and variable working distance system 663. Surgical camera 660 may be communicatively coupled with surgical camera system 685 and display 690. Surgical camera system 685 may include image processing system 670, processor 680, and memory medium 681.

Display 690 may be a head-up display mounted on support member 698 and mount base 699. Support member 698 and mount base 699 may be adjustable to change the distance between display 690 and the surgeon. Display 690 may also be ceiling mounted. Display 690 may be communicatively coupled with surgical camera system 685. Display 690 may be a picture-in-picture display. In another example, surgical camera 660 may be a 3D HDR camera and display 690 may be a 3D 4K OLED surgical display. Display 690 may display a 3D surgical image of an eye. Processor 680 may be an ultra-high-speed 3D image processor, which may optimize 3D HDR images in real time.

Surgical camera 660 may be communicatively coupled with surgical camera system 685 and display 690. Display 690 may receive information from surgical camera 660 via surgical camera system 685. Display 690 may display a digital image of an eye captured by surgical camera 660.

Surgeon head movement detection device 650 may detect a head movement of surgeon 101 and send a signal corresponding to the detected head movement to processor 680. The head movement of surgeon 101 may be analyzed by intelligent tracking system 271. The head movement of surgeon 101 may be pitch 110, yaw 120, roll 130, x 140, z 150, y 160, or any combination thereof. The head movement of surgeon 101 may be described by Cartesian co-ordinates corresponding to x-axis 111, z-axis 121 and y-axis 131.

Intelligent tracking system 271 may execute instructions on processor 680 to determine if the head movement of surgeon 101 corresponds to a defined head movement. Intelligent tracking system 271 may include noise detection system 272, motion thresholding system 273, and motion recognition system 274. Intelligent tracking system 271 may allow a head tracking control system to control surgical camera 660 when surgeon 101 makes a defined head movement. A defined head movement may include a quiet head movement, a deliberate head movement, an uncommon head movement, or any combination thereof. A defined head movement may correspond to a characteristic movement of marker 635 detected by surgeon head movement detection device 650.

Processor 680 may execute instructions to move surgical camera 660 in response to the defined head movement of surgeon 101. Movement of surgical camera 660 may be described by Cartesian co-ordinates corresponding to x-axis 611, z-axis 621 and y-axis 631. Visualization system 600 may maintain a relative pose in six degrees of freedom (x, y, z, pitch, yaw, and roll) between the head of surgeon 101 (x-axis 111, z-axis 121 and y-axis 131) and surgical camera 660 (x-axis 611, z-axis 621 and y-axis 631). In this way, surgical camera 660 may function as if it were attached to the head of surgeon 101 when a head tracking control system is activated. The surgical camera 660 may be a distance 666 from the head of surgeon 101. Distance 666 may be in a range of from about 175 mm to about 300 mm. When the head tracking control system is activated, surgeon 101 may move his head as if it were surgical camera 660. The head tracking control system may be activated, for example, by a foot pedal.

Intelligent tracking system 271 may allow a head tracking control system to control surgical camera 660 if surgeon 101 makes a defined head movement that is a quiet head movement, a deliberate head movement, and an uncommon head movement. Alternatively, intelligent tracking system 271 may allow a head tracking control system to control surgical camera 660 if surgeon 101 makes a defined head movement that is a quiet head movement, a deliberate head movement, an uncommon head movement, or any combination thereof. Accordingly, a surgeon head movement that is not a defined head movement may be ignored by a head tracking control system in visualization system 600. A defined head movement when controlling surgical camera 660 may be different to a defined head movement when controlling ophthalmic surgical microscope 201.

In another example, processor 680 may execute instructions to allow navigation on display 690 in response to a defined head movement of surgeon 101. Display 690 may display a virtual display of a surgical procedure. A head movement of surgeon 101 that is pitch 110 or yaw 120 may be used to navigate around the virtual display. Alternatively, a head movement of surgeon 101 that is pitch 110 or yaw 120 may be used to execute commands of yes and no, respectively to navigate on display 690.

Figure 7:
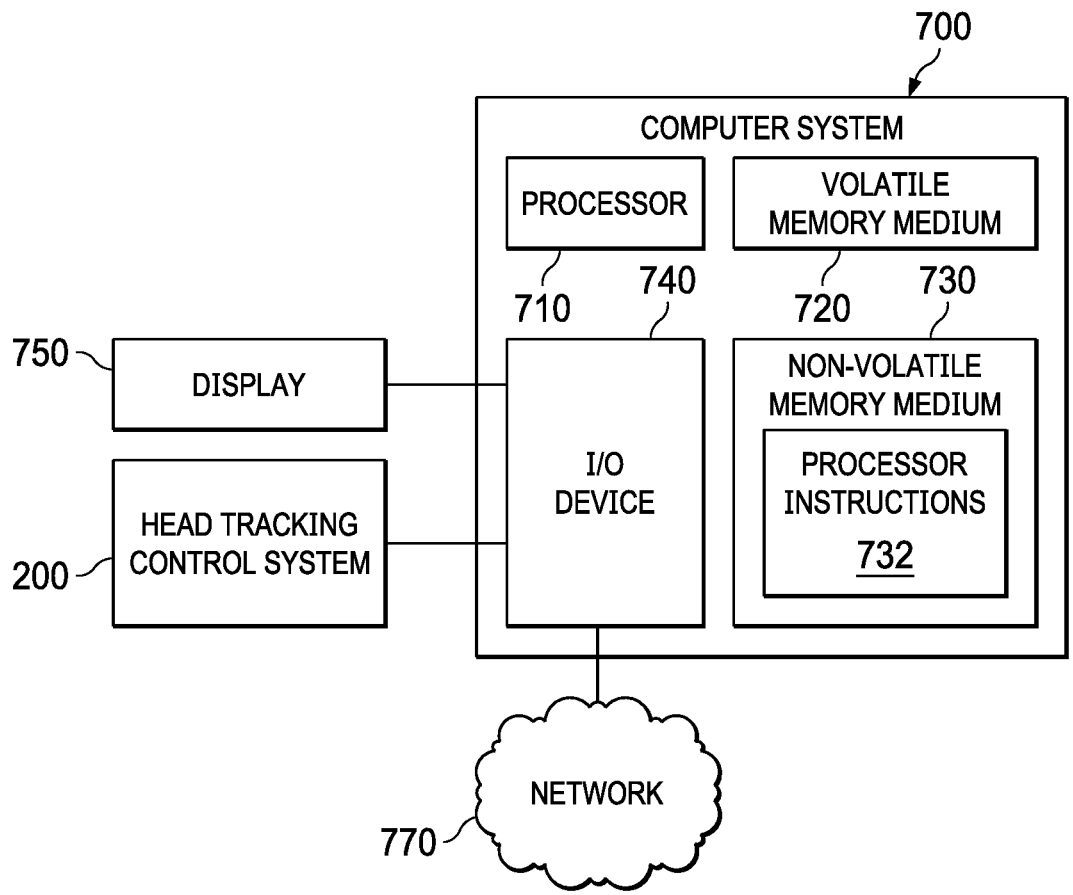
FIG. 7 is a schematic representation of a computer system, including a head tracking control system.

Head tracking control system 200, head tracking control system 400, or head tracking control system 500 may be used in combination with a computer system 700, as depicted in FIG. 7. Computer system 700 may include a processor 710, a volatile memory medium 720, a non-volatile memory medium 730, and an input/output (I/O) device 740. Volatile memory medium 720, non-volatile memory medium 730, and I/O device 740 may be communicatively coupled to processor 710.

The term "memory medium" may mean a "memory", a "storage device", a "memory device", a "computer-readable medium", and/or a "tangible computer readable storage medium". For example, a memory medium may include, without limitation, storage media such as a direct access storage device, including a hard disk drive, a sequential access storage device, such as a tape disk drive, compact disk (CD), random access memory (RAM), read-only memory (ROM), CD-ROM, digital versatile disc (DVD), electrically erasable programmable read-only memory (EEPROM), flash memory, non-transitory media, or any combination thereof. As shown in FIG. 7, non-volatile memory medium 730 may include processor instructions 732. Processor instructions 732 may be executed by processor 710. In one example, one or more portions of processor instructions 732 may be executed via non-volatile memory medium 730. In another example, one or more portions of processor instructions 732 may be executed via volatile memory medium 720. One or more portions of processor instructions 732 may be transferred to volatile memory medium 720.

Processor 710 may execute processor instructions 732 in implementing at least a portion of one or more systems, one or more flow charts, one or more processes, and/or one or more methods described herein. For example, processor instructions 732 may be configured, coded, and/or encoded with instructions in accordance with at least a portion of one or more systems, one or more flowcharts, one or more methods, and/or one or more processes described herein. Although processor 710 is illustrated as a single processor, processor 710 may be or include multiple processors. One or more of a storage medium and a memory medium may be a software product, a program product, and/or an article of manufacture. For example, the software product, the program product, and/or the article of manufacture may be configured, coded, and/or encoded with instructions, executable by a processor, in accordance with at least a portion of one or more systems, one or more flowcharts, one or more methods, and/or one or more processes described herein.

Processor 710 may include any suitable system, device, or apparatus operable to interpret and execute program instructions, process data, or both stored in a memory medium and/or received via a network. Processor 710 further may include one or more microprocessors, microcontrollers, FPGAs, DSPs, ASICs, or other circuitry configured to interpret and execute program instructions, process data, or both.

I/O device 740 may include any instrumentality or instrumentalities, which allow, permit, and/or enable a user to interact with computer system 700 and its associated components by facilitating input from a user and output to a user. Facilitating input from a user may allow the user to manipulate and/or control computer system 700, and facilitating output to a user may allow computer system 700 to indicate effects of the user's manipulation and/or control. For example, I/O device 740 may allow a user to input data, instructions, or both into computer system 700, and otherwise manipulate and/or control computer system 700 and its associated components. I/O devices may include user interface devices, such as a keyboard, a mouse, a touch screen, a joystick, a handheld lens, a tool tracking device, a coordinate input device, or any other I/O device suitable to be used with a system.

I/O device 740 may include one or more buses, one or more serial devices, and/or one or more network interfaces, among others, that may facilitate and/or permit processor 710 to implement at least a portion of one or more systems, processes, and/or methods described herein. In one example, I/O device 740 may include a storage interface that may facilitate and/or permit processor 710 to communicate with an external storage. The storage interface may include one or more of a universal serial bus (USB) interface, a SATA (Serial ATA) interface, Ethernet, a PATA (Parallel ATA) interface, and a small computer system interface (SCSI), among others. In a second example, I/O device 740 may include a network interface that may facilitate and/or permit processor 710 to communicate with a network. I/O device 740 may include one or more of a wireless network interface and a wired network interface. In a third example, I/O device 740 may include one or more of a peripheral component interconnect (PCI) interface, a PCI Express (PCIe) interface, a serial peripheral interconnect (SPI) interface, and an inter-integrated circuit (I2C) interface, among others. In a fourth example, I/O device 740 may include circuitry that may permit processor 710 to communicate data with one or more sensors. In a fifth example, I/O device 740 may facilitate and/or permit processor 710 to communicate data with one or more of a display 750 and head tracking control system 200, among others. As shown in FIG. 7, I/O device 740 may be coupled to a network 770. For example, I/O device 740 may include a network interface.

Network 770 may include a wired network, a wireless network, an optical network, or any combination thereof. Network 770 may include and/or be coupled to various types of communications networks. For example, network 770 may include and/or be coupled to a local area network (LAN), a wide area network (WAN), an Internet, a public switched telephone network (PSTN), a cellular telephone network, a satellite telephone network, or any combination thereof. A WAN may include a private WAN, a corporate WAN, a public WAN, or any combination thereof.

Although FIG. 7 illustrates computer system 700 as external to head tracking control system 200, head tracking control system 200 may include computer system 700. For example, processor 710 may be or include processor 280.

Figure 8A:
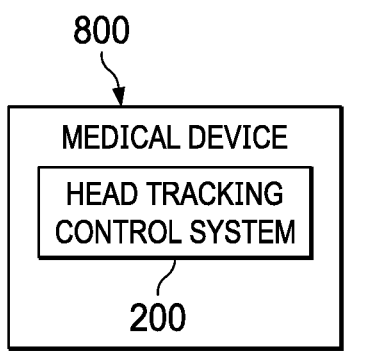
FIGS. 8A-8C are schematic representations of a medical system, including a head tracking control system.
Figure 8B:
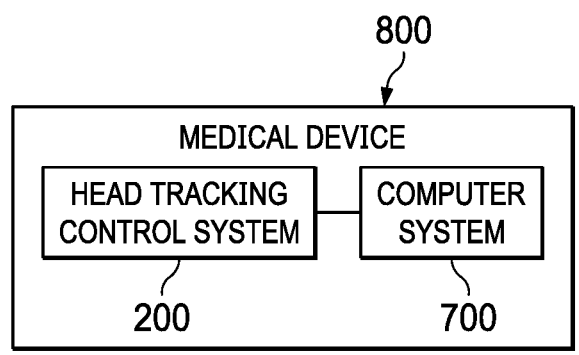
Figure 8C:
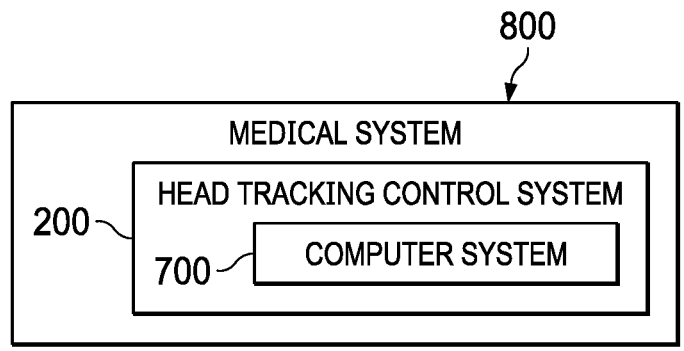

FIGS. 8A-8C illustrate examples of medical system 800. As shown in FIG. 8A, medical system 800 may include head tracking control system 200. Alternatively, medical system 800 may include head tracking control system 400 or head tracking control system 500. As illustrated in FIG. 8B, medical system 800 may include head tracking control system 200 and computer system 700. Head tracking control system 200 may be communicatively coupled with computer system 700. As shown in FIG. 8C, medical system 800 may include head tracking control system 200, which may include computer system 700.

Figure 9:
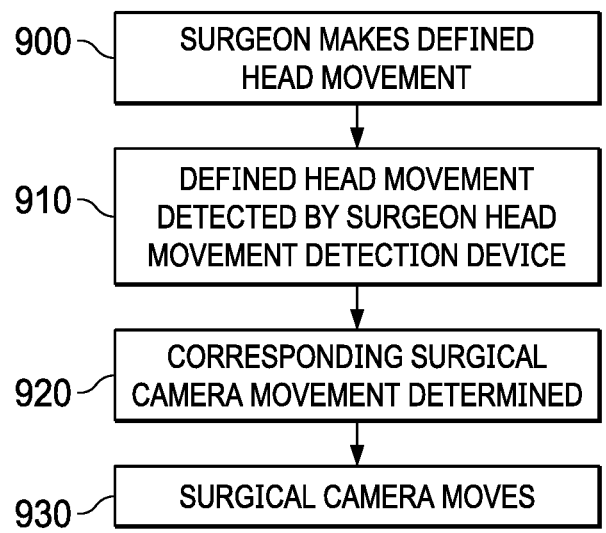
FIG. 9 is a flow diagram illustrating a method of controlling a visualization system using a head tracking control system.

FIG. 9 presents a flow diagram for a method of controlling a visualization system using a head tracking control system. In step 900, a surgeon makes a defined head movement, which may be a head movement that is a quiet head movement, a deliberate head movement, and an uncommon head movement. In step 910, the defined head movement may be detected by a surgeon head movement detection device, such as surgeon head movement detection device 650. The defined head movement may be pitch 110, yaw 120, roll 130, x 140, z 150, y 160, or any combination thereof. In step 920, a corresponding movement of a surgical camera, such as surgical camera 660, may be determined. The corresponding movement of the surgical camera may be in six degrees of freedom. Alternatively, the corresponding movement of the surgical camera may be in less than six degrees of freedom. For example, head tracking control system 200 may detect a defined head movement of the surgeon in six degrees of freedom, but may control ophthalmic surgical microscope 201 in three degrees of freedom. In step 930, the surgical camera may move in response to the defined head movement of the surgeon.

Head tracking control system 200, head tracking control system 400, head tracking control system 500, visualization system 600, computer system 700, medical system 800, and components thereof may be combined with other elements of visualization tools and systems described herein unless clearly mutually exclusive. For instance, the infrared camera and active infrared illuminator may be used with other visualization systems described herein.

The above disclosed subject matter is to be considered illustrative, and not restrictive, and the appended claims are intended to cover all such modifications, enhancements, and other embodiments which fall within the true spirit and scope of the present disclosure. For example, although a head tracking control system is most commonly needed to improve control of a visualization system for ophthalmic surgery, if it were useful in another procedure, such as a purely diagnostic procedure not otherwise considered to be surgery, the systems and methods described herein may be employed.

The invention claimed is:

1. A head tracking control system comprising:
    at least one marker operable to be positioned on a head of a surgeon;
    an infrared camera comprising at least two infrared sensors and operable to:
        detect infrared light reflected off the at least one marker and send a signal corresponding to the detected light to a processor; and
        execute instructions on the processor to detect a movement of the at least one marker;
    an intelligent tracking system operable to execute instructions on the processor to determine if the detected movement of the at least one marker corresponds to a defined head movement of the surgeon, wherein a head movement that is not the defined head movement is ignored by the head tracking control system; and
    an ophthalmic surgical microscope comprising the processor, wherein, if the detected movement of the at least one marker corresponds to the defined head movement of the surgeon, the processor is operable to execute instructions to control the ophthalmic surgical microscope.

2. The head tracking control system of claim 1, wherein the defined head movement of the surgeon is a quiet head movement, a deliberate head movement, an uncommon head movement, or any combination thereof.

3. The head tracking control system of claim 1, wherein the intelligent tracking system comprises:
    a noise detection system comprising a microphone and operable to determine if the detected movement of the at least one marker corresponds to a quiet head movement of the surgeon;
    a motion thresholding system operable to determine if the detected movement of the at least one marker corresponds to a deliberate head movement of the surgeon; and
    a motion recognition system operable to determine if the detected movement of the at least one marker corresponds to an uncommon head movement of the surgeon.

4. The head tracking control system of claim 1, wherein the defined head movement is a displacement along an x-axis, a displacement along a y-axis, a pitch movement, or any combination thereof.

5. The head tracking control system of claim 1, further comprising a motorized microscope head support; and
    wherein the processor is operable to control the ophthalmic surgical microscope by executing instructions to move the motorized microscope head support along a microscope movement x-axis, a microscope movement y-axis, or any combination thereof.

6. The head tracking control system of claim 1, further comprising an objective; and
   wherein the processor is operable to control the ophthalmic surgical microscope by executing instructions to move the objective.

7. The head tracking control system of claim 1, wherein the at least one marker is an active infrared marker, a passive infrared marker, a fiducial marker, disposed in a cap, attached by adhesive, marked in pen, or any combination thereof.

8. A head tracking control system comprising:
   a 3-axis gyroscope and a 3-axis accelerometer operable to be positioned on the head of a surgeon and operable to detect a head movement of the surgeon and send a signal corresponding to the detected movement to a processor;
   an intelligent tracking system operable to execute instructions on the processor to determine if the detected head movement of the surgeon corresponds to a defined head movement of the surgeon, wherein a head movement that is not the defined head movement is ignored by the head tracking control system; and
   an ophthalmic surgical microscope comprising the processor, wherein, if the detected head movement of the surgeon corresponds to the defined head movement of the surgeon, the processor is operable to execute instructions to control the ophthalmic surgical microscope.

9. The head tracking control system of claim 8, wherein the defined head movement of the surgeon is a quiet head movement, a deliberate head movement, an uncommon head movement, or any combination thereof.

10. The head tracking control system of claim 8, wherein the intelligent tracking system comprises:
    a noise detection system comprising a microphone and operable to determine if the detected head movement of the surgeon corresponds to a quiet head movement;
    a motion thresholding system operable to determine if the detected head movement of the surgeon corresponds to a deliberate head movement; and
    a motion recognition system operable to determine if the detected head movement of the surgeon corresponds to an uncommon head movement.

11. The head tracking control system of claim 8, wherein the defined head movement is a displacement along an x-axis, a displacement along a y-axis, a pitch movement, or any combination thereof.

12. The head tracking control system of claim 8, further comprising a motorized microscope head support; and
    wherein the processor is operable to control the ophthalmic surgical microscope by executing instructions to move the motorized microscope head support along a microscope movement x-axis, a microscope movement y-axis, or any combination thereof.

13. The head tracking control system of claim 8, further comprising an objective; and
    wherein the processor is operable to control the ophthalmic surgical microscope by executing instructions to move the objective.

14. A visualization system comprising:
    a head tracking control system comprising
    a) a processor;
    b) at least one marker operable to be positioned on a head of a surgeon;
    c) a surgeon head movement detection device operable to:
       detect infrared light reflected off the at least one marker and send a signal corresponding to the detected light to the processor; and
       execute instructions on the processor to detect a movement of the at least one marker; and
    d) an intelligent tracking system operable to execute instructions on the processor to determine if the detected movement of the at least one marker corresponds to a defined head movement of the surgeon; and
    a surgical camera operable to:
    move with six degrees of freedom; and
    be controlled by the processor if the movement of the at least one marker corresponds to the defined head movement of the surgeon, wherein a head movement that is not the defined head movement is ignored by the head tracking control system.

15. The visualization system of claim 14, wherein the surgical camera is a component of an NGENUITY® 3D Visualization System.

16. The visualization system of claim 14, wherein the defined head movement of the surgeon is a quiet head movement, a deliberate head movement, an uncommon head movement, or any combination thereof.

17. The visualization system of claim 14, wherein the intelligent tracking system comprises:
    a noise detection system comprising a microphone and operable to determine if the detected movement of the at least one marker corresponds to a quiet head movement of the surgeon;
    a motion thresholding system operable to determine if the detected movement of the at least one marker corresponds to a deliberate head movement of the surgeon; and
    a motion recognition system operable to determine if the detected movement of the at least one marker corresponds to an uncommon head movement of the surgeon.

18. The visualization system of claim 14, wherein the defined head movement is a displacement along an x-axis, a displacement along a y-axis, a pitch movement, or any combination thereof.

19. The visualization system of claim 14, wherein the at least one marker is an active infrared marker, a passive infrared marker, a fiducial marker, disposed in a cap, attached by adhesive, marked in pen, or any combination thereof.

* * * * *